(12) United States Patent
Börmann et al.

(10) Patent No.: US 10,221,166 B2
(45) Date of Patent: Mar. 5, 2019

(54) PROCESS FOR STRETCHING A FILM WEB

(75) Inventors: Ludwig Börmann, Babensham (DE); Günter Schreiner, Schnaitsee (DE)

(73) Assignee: RKW SE, Frankenthal (DE)

( * ) Notice: Subject to any disclaimer, the term of this patent is extended or adjusted under 35 U.S.C. 154(b) by 1202 days.

(21) Appl. No.: 14/240,697

(22) PCT Filed: Aug. 30, 2012

(86) PCT No.: PCT/EP2012/066880
§ 371 (c)(1),
(2), (4) Date: May 6, 2014

(87) PCT Pub. No.: WO2013/030290
PCT Pub. Date: Mar. 7, 2013

(65) Prior Publication Data
US 2014/0248484 A1 Sep. 4, 2014

(30) Foreign Application Priority Data
Sep. 2, 2011 (EP) ..................... 11179885

(51) Int. Cl.
*C07D 417/04* (2006.01)
*C07D 417/06* (2006.01)
(Continued)

(52) U.S. Cl.
CPC ........ *C07D 417/06* (2013.01); *A61F 13/0226* (2013.01); *A61F 13/0276* (2013.01);
(Continued)

(58) Field of Classification Search
CPC ......... B29C 55/005; B29C 55/06; B32B 7/02; B32B 27/08; B32B 27/36; B32B 27/30;
(Continued)

(56) References Cited

U.S. PATENT DOCUMENTS 3,548,048 A 12/1970 Hughes et al.
4,880,422 A * 11/1989 McBride ........... A61F 13/15203
604/389

(Continued)

FOREIGN PATENT DOCUMENTS

DE 3326056 A1 1/1984
EP 0256885 A2 2/1988
(Continued)

OTHER PUBLICATIONS

International Search Report and Written Opinion for PCT/EP2012/066880 dated Mar. 1, 2013.
(Continued)

*Primary Examiner* — Jeffrey M Wollschlager
(74) *Attorney, Agent, or Firm* — McCarter & English, LLP; Steven G. Davis; Wei Song

(57) ABSTRACT

The invention relates to a process for the stretching of a starting film web of thermoplastic polymer material, which comprises at least one low-melting polymer component and at least one high-melting polymer component, the process comprising at least the following steps: heating of the starting film web to an at least partly molten state in which the at least one low-melting polymer component exists in a molten liquid state and the at least one high-melting polymer component does not exist in the molten liquid state, by at least one heating roller and cooling down by passing the partly molten film web through a cooled roller nip, the film being stretched between the at least one heating roller and the cooled roller nip. The films produced may be laminated together with a non-woven fabric.

11 Claims, 1 Drawing Sheet

(51) Int. Cl.
| | |
|---|---|
| B29C 55/00 | (2006.01) |
| B29C 55/06 | (2006.01) |
| A61F 13/15 | (2006.01) |
| B32B 27/32 | (2006.01) |
| A61F 13/514 | (2006.01) |
| A61F 13/02 | (2006.01) |
| B32B 37/20 | (2006.01) |
| B32B 38/00 | (2006.01) |
| B32B 5/02 | (2006.01) |
| B32B 27/12 | (2006.01) |
| B32B 7/02 | (2019.01) |
| B32B 27/08 | (2006.01) |
| B32B 27/30 | (2006.01) |
| B32B 27/36 | (2006.01) |
| B29K 23/00 | (2006.01) |
| B29L 31/48 | (2006.01) |
| B32B 37/06 | (2006.01) |
| B32B 37/08 | (2006.01) |

(52) U.S. Cl.
CPC .. *A61F 13/15731* (2013.01); *A61F 13/51401* (2013.01); *A61F 13/51464* (2013.01); *B29C 55/005* (2013.01); *B29C 55/06* (2013.01); *B32B 5/022* (2013.01); *B32B 7/02* (2013.01); *B32B 27/08* (2013.01); *B32B 27/12* (2013.01); *B32B 27/30* (2013.01); *B32B 27/32* (2013.01); *B32B 27/36* (2013.01); *B32B 37/203* (2013.01); *B32B 38/0012* (2013.01); *C07D 417/04* (2013.01); *A61F 2013/51409* (2013.01); *B29K 2023/0625* (2013.01); *B29K 2023/0633* (2013.01); *B29K 2023/10* (2013.01); *B29K 2023/14* (2013.01); *B29L 2031/4878* (2013.01); *B32B 37/06* (2013.01); *B32B 37/08* (2013.01); *B32B 2038/0028* (2013.01); *B32B 2250/42* (2013.01); *B32B 2274/00* (2013.01); *B32B 2305/20* (2013.01); *B32B 2309/02* (2013.01); *B32B 2323/04* (2013.01); *B32B 2323/10* (2013.01); *B32B 2555/00* (2013.01); *B32B 2555/02* (2013.01); *Y10T 442/678* (2015.04)

(58) Field of Classification Search
CPC ....... B32B 27/12; B32B 5/022; B32B 37/203; B32B 38/0012; B32B 27/32; B32B 2250/42; B32B 2274/00; B32B 2555/00; B32B 2323/10; B32B 2323/04; B32B 2305/20; B32B 37/08; B32B 37/06; B32B 2038/0028; B32B 2309/02; B32B 2555/02; A61F 13/51464; A61F 13/0226; A61F 13/0276; A61F 13/51401; A61F 13/15731; A61F 2013/51409; Y10T 442/678; B29K 2023/14; B29K 2023/0633; B29K 2023/0625; B29K 2023/10; B29L 2031/4878
See application file for complete search history.

(56) References Cited

U.S. PATENT DOCUMENTS

| | | | | |
|---|---|---|---|---|
| 5,084,039 | A * | 1/1992 | Cancio | A61F 13/51401 525/209 |
| 5,169,712 | A * | 12/1992 | Tapp | B32B 5/22 428/315.5 |
| 5,707,478 | A * | 1/1998 | Fujii | B29C 47/0021 156/309.9 |
| 6,383,431 | B1 * | 5/2002 | Dobrin | B29C 55/14 156/229 |
| 6,403,505 | B1 * | 6/2002 | Groitzsch | B32B 7/04 428/198 |
| 7,947,147 | B2 * | 5/2011 | Bormann | A61F 13/514 156/229 |
| 8,163,216 | B2 | 4/2012 | Bormann et al. | |
| 2003/0213549 | A1 * | 11/2003 | McAmish | B29C 55/023 156/229 |
| 2003/0216518 | A1 | 11/2003 | Tau et al. | |
| 2004/0121690 | A1 * | 6/2004 | Mleziva | A61F 13/4902 442/381 |
| 2006/0025737 | A1 * | 2/2006 | Song | A61F 13/15203 604/385.01 |
| 2006/0041239 | A1 * | 2/2006 | Nagahara | A61F 13/15203 604/380 |
| 2006/0148358 | A1 * | 7/2006 | Hall | B32B 5/022 442/328 |
| 2007/0116953 | A1 * | 5/2007 | English | D02G 3/06 428/397 |
| 2007/0254158 | A1 * | 11/2007 | Bormann | A61F 13/514 428/411.1 |
| 2008/0131681 | A1 * | 6/2008 | Bormann | A61L 15/225 428/220 |
| 2009/0258138 | A1 * | 10/2009 | Burmester | B05B 7/0861 427/207.1 |
| 2010/0022978 | A1 * | 1/2010 | Kasai | A61F 13/15658 604/367 |

FOREIGN PATENT DOCUMENTS

| | | |
|---|---|---|
| EP | 0452813 A2 | 10/1991 |
| EP | 0616880 A2 | 9/1994 |
| EP | 0768168 A2 | 4/1997 |
| EP | 0951080 A1 | 10/1999 |
| EP | 1716830 A1 | 11/2006 |
| GB | 2152516 A | 8/1985 |
| WO | 9532089 A1 | 11/1995 |
| WO | WO-01/009424 A1 | 2/2001 |
| WO | WO-2003/008190 A1 | 1/2003 |
| WO | WO-2004/094129 A2 | 11/2004 |
| WO | WO-2007/078568 A2 | 7/2007 |
| WO | WO-2010/112418 A1 | 10/2010 |
| WO | WO-2010/128124 A1 | 11/2010 |

OTHER PUBLICATIONS

Search Report for EP priority application No. 11179885.6 dated Jun. 25, 2012.
Yamada, Toshiro (edited by Kanai et al.). "Film Processing". Hanser/Gardner Publications, 1999. pp. 181-209.
English translation of EP Application No. 96116322.7 filed Oct. 11, 1996; published as EP 0 768 168 A2 dated Apr. 16, 1997; Applicant: BP Chemicals PlasTec GmbH.

* cited by examiner

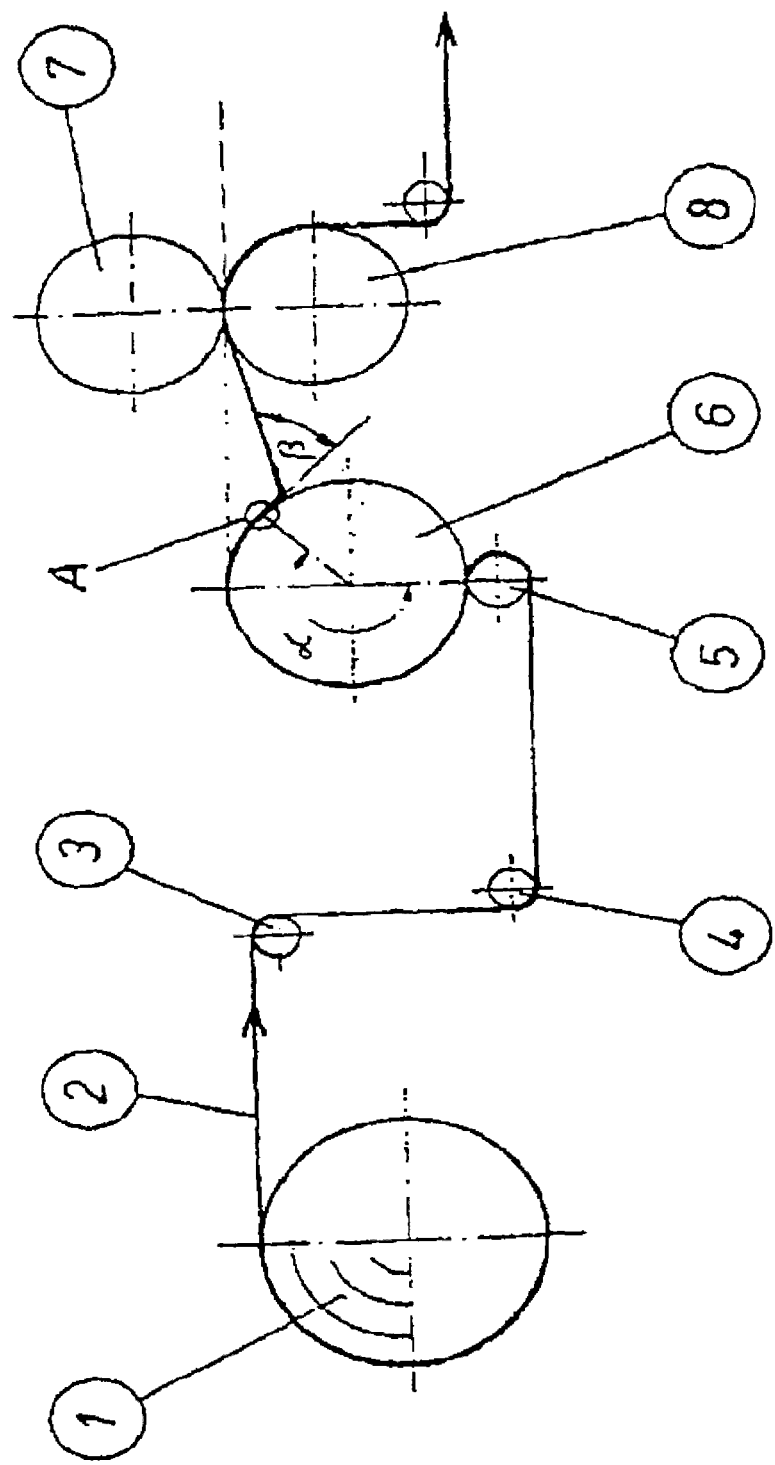

PROCESS FOR STRETCHING A FILM WEB

This application is a 35 U.S.C. § 371 national stage filing of International Application No. PCT/EP2012/066880, filed Aug. 30, 2012, which claims the benefit of European Patent Application No. 11179885.6, filed Sep. 2, 2011. The entire teachings of the each of the foregoing patent applications are expressly incorporated herein by reference.

The invention relates to processes for stretching a film web for the manufacture of very thin films and processes for manufacturing of non-woven fabric-film laminates, film webs and non-woven fabric-film laminates produced thereby, as well as their use, for example, in the hygiene field.

In the context of environmental debates concerning conserving resources and sustainability, it is becoming of ever-increasing importance in the context of films, particularly of films for disposable products in the hygiene sector, to produce even thinner films than in the past, in order to save raw materials.

From EP-A-0 768 168 and EP-A-1 716 830 processes for the manufacture of films usable in the hygiene field are known. Having regard to their field of use, such hygiene films are required to meet several requirements. They are to be liquid-impervious and comply with certain haptic properties, such as softness, flexibility, low-rustling performance and textile feel. Films in the hygiene field should have a soft, cloth-like feel. In particular, when to be used for incontinence products, they should give rise to as little noise as possible, that is to say, the films should give rise to low rustling levels. In combination with a low shininess, this results in a very textile-like film, as is desirable in the hygiene field. An additional factor is that in recent years the absorption bodies contained in diapers and incontinence products have become progressively thinner, made possible particularly by the use of super-absorber polymers. These super-absorber polymers are employed in the form of coarsely-particulate powders, and the hygiene films must be sufficiently strong to prevent with certainty perforation of the film by the individual particles, e.g. when subjected to loads by sitting down or other movements of the wearer. A formation of punched holes ("pinholes"), due to super-absorber polymers and a bursting of the completed film products in the packaging units must be avoided. A further requirement for hygiene films resides in a minimum tensile strength as needed for processing the film webs in the very fast-running machines (converters) of the manufacturers of e.g. diapers and sanitary napkins. This minimum tensile strength is specified in terms of 5%, 10% or 25% stretching in the machine direction (md) or transverse direction (cd). At present, the tensile strength at 5% stretching (5%-modulus) in the machine direction should be at least 2.5 N/inch. In addition to that, films for hygiene uses should provide a longitudinal and transverse tearing strength of at least 10 N/inch.

Also known is the use of laminates of film and non-woven fabrics. A manufacture of such laminates is described in WO 2006/024394, in which a starting film web of thermoplastic polymer material is heated jointly with a starting non-woven textile web, the melting point of which is above the crystallite melting point of the polymer material, to a temperature above the crystallite melting point of the polymer material and below the melting point of the starting non-woven fabric web, and the laminate formed is passed through a cooled roller nip and in the course thereof is cooled to a temperature below the crystallite melting point of the starting film web.

In EP-A-0 768 168 a starting film web of thermoplastic polymer material is heated to a liquid molten state of the polymer material and thereafter passed through a cooled roller nip. In EP-A-1 716 830 a process, including heating the polymer material and subsequent passage through a cooled roller nip, is performed with a starting film web which contains a thermoplastic polymer material, including a polyethylene-matrix, in which are contained 1 to 70 parts by weight of polypropylene, based on 100 parts by weight of polyethylene-matrix. In this, heating of the starting film web up to the liquid molten state of the polyethylene-matrix material is performed, however not up to the liquid molten state of the polypropylene. Films are there described having low thicknesses down to 15 μm, which still comply with the requirements of hygiene films. According to the state of the art, stretching or drawing out of film webs is known in order to reduce the thickness of films. Thus, from published specification DE 1 108 420 a process is known for the manufacture of thermoplastic films, according to which drawing out of the film in all directions is performed, wherein the drawing out is carried out in a temperature range from the crystallite melting point or softening point down to 60° C. below those points. The laid-open specification DE 1 704 538 relates to a process for the mono-axial stretching of polypropylene films, in which the stretching is performed in two or more successive stages whilst maintaining specific reaction conditions up to a final extension ratio of 6:1. The laid-open specification DE 2 257 089 describes a process for mono-axially stretching thermoplastic films, in which a reduction of the web widths is avoided and a uniform film is attained in that, during the stretching procedure, softening heat is applied to the film in a defined manner. DE 600 08 145 T2 concerns a process for stretching a film, for example a thermoplastic film, in which an apparatus with driven and non-driven holding means is employed. Resulting non-uniformities of the holding means spacings in this context are to be minimised by a particular manner of cooling.

Accordingly, it is the object of the invention to produce even thinner films than are obtainable, for example, according to EP-A-1 716 830, in order to save on raw materials, and which can be further processed into hygiene products.

According to the invention, it was found that films of thermoplastic polymer material, which contain a low-melting component and a high-melting component, can surprisingly be extensively stretched, if they are transformed by heating into a partly-molten state, such that the low-melting component, but not the high-melting component, exists in the liquid molten state, and subsequently cooling is performed in a cooled roller nip. In this context, the stretching is brought about between a heating roller employed for the heating and the cooling roller nip. In this manner, it is possible to attain a significant reduction of the film thickness. This makes possible a manufacture under stable process conditions of ultra-thin films having thicknesses down to 5 μm or 4 g/m² respectively, or even less, and results in economically-attractive raw material savings. It was surprising that by heating the film web to the partly-liquid molten condition such extensive stretching is possible.

Thus, the invention relates to a process for the stretching of a starting material film web of thermoplastic polymer material, which comprises at least one low-melting polymer component and at least one high-melting polymer component, the process comprising at least the following steps: heating of the starting film web to an at least partly molten state in which the at least one low-melting polymer component exists in a molten liquid state and the at least one high-melting polymer component does not exist in the molten liquid state, by at least one heating roller and cooling down by passing the partly molten film web through a cooled roller nip, the film web being stretched between the at least one heating roller and the cooled roller nip.

In a preferred embodiment of the invention, the cooling rollers forming the cooled roller nip are driven at a higher velocity than the at least one heating roller.

In a further preferred embodiment of the invention, two rollers upstream of the cooling roller nip are provided, which are driven at different velocities, such that the film web is stretched between the first and the second roller and wherein at least the first of the two rollers is designed as a heating roller. In a preferred further development of this embodiment, it is possible, if apart from the first roller, the second roller as well is designed as a heating roller, that, in addition, a non-woven fabric web may jointly be passed over this second heating roller and be passed jointly with the film web through the cooled roller nip, such that a non-woven fabric-film laminate is obtained.

Furthermore, the invention relates to a non-woven fabric-film laminate, which is produced by adhesively bonding a film obtained according to the invention to a non-woven fabric.

Furthermore, the invention relates to the film webs and laminates produced by way of the described process, as well as their use, in particular in the hygiene or medical sector. Preferred embodiments of the invention are described in the now following description, the drawing, the example and in the subsidiary claims.

The process according to the invention enables the manufacture of extremely thin commercially and technically usable films. For example, films may be manufactured having a thickness of less than 10 μm, e.g. 8 μm or 6 μm or 5 μm or even less, for example 2 μm, in a stable process. Such films may, e.g. in-line, be further processed into laminates for use as so-called back sheets with textile feel (textile back sheets) for diapers. A further advantage of the film webs produced according to the process of the invention resides in an improved thermo-stability, due to the employment of the high-melting polymer component, e.g. of polypropylene. For example, in the use of the film webs as back sheets in the hygiene sector, this enables the internal fillings of e.g. baby diapers or incontinence articles to be applied by means of hot-melt adhesive systems at temperatures in the range of 140 to 160° C. without the thin film back sheet thereby being partly melted.

In the context of the present invention, the stated melting points, melting ranges and crystallite melting points relate to a determination according to DSC (Differential Scanning calorimetry).

According to the invention, the starting film web contains or comprises at least one low-melting polymer component and at least one high-melting polymer component. In other words, the starting film web contains one or more low-melting polymer component(s) and one or more high-melting polymer component(s). The same meanings apply to the terms used below in the context of the invention "a low-melting polymer component" and "a high-melting polymer component", i.e. these as well include one or more low-melting or respectively high-melting polymer component(s). Preferably, the starting film web contains one, or preferably two, low-melting polymer component(s). Preferably, it contains one, more particularly two, high-melting polymer component(s). In other embodiments of the invention, it contains preferably three low-melting polymer components and/or three high-melting polymer components. Whether a polymer material of the starting film web is to be considered a low-melting polymer component or a high-melting polymer component is determined according to the invention in terms of the respective crystallite melting point, melting point or melting range of the polymer material in relation to the stretching temperature. At a given stretching temperature, the liquid molten polymer materials are assigned to the low-melting polymer component and the non-liquid molten polymer materials to the high-melting polymer component.

It is well known that polymers have no sharply-defined melting point, but a melting range, even though it is possible to assign a crystallite melting point to the crystalline regions of a polymer. This crystallite melting point is always higher than the melting point or melting range of the non-crystalline components. The liquid molten state is defined by the state in which the shear modulus approaches zero. In the case of polymers having crystalline regions, the latter are then no longer detectable. The shear modulus may, for example, be determined according to ISO 6721-1 & 2. In the present invention the starting film web is heated to a temperature at which the shear modulus of the low-melting polymer component is zero and for the high-melting polymer component the shear modulus is not zero. At that stage, no crystalline regions are detectable any more for the low-melting polymer component and the low-melting polymer component is present in its liquid molten state. On the other hand, for the high-melting polymer component crystalline regions are still detectable and that polymer component is below the liquid molten state. To summarise, the shear modulus of the whole polymer material of the starting film web is accordingly not zero and crystalline regions of the high-melting polymer component are still detectable. Accordingly, there now exists a partly-molten film web.

In principle, all thermoplastic polymers can be used, which have the appropriate melting points to serve as materials for the two polymer components of the starting film web. For this purpose, numerous commercial products are commercially-available. Preferably, a variety of polyolefins, in particular polyethylenes, polypropylenes, copolymers of ethylene and propylene, co-polymers of ethylene and propylene with other comonomers, or mixtures thereof are employed. Furthermore, ethylene vinyl acetate (EVA), ethylene acrylate (EA), ethylene ethyl acrylate (EEA), ethylene acrylic acid (EAA), ethylene methyl acrylate (EMA), ethylene butyl acrylate (EBA), polyesters (PET), polyamides (PA), e.g. nylon, ethylene vinyl alcohols (EVOH), polystyrene (PS), polyurethane (PU) or thermoplastics olefin elastomers are suitable.

The total amount of low-melting polymer component is preferably 90 to 30% by weight, in particular 80 to 40% by weight, most preferably 70 to 50% by weight, and the total amount of high-melting polymer component is preferably 10 to 70% by weight, in particular 20 to 60% by weight, most preferably 30 to 50% by weight, each based on 100% by weight of low-melting and high-melting polymer components. In the alternative, the total amount of low-melting polymer component is 85 to 15% by weight and the total amount of high-melting polymer component is 15 to 85% by weight, again based on 100% by weight of low-melting and high-melting components. These quantitative data apply, for example, in the case of the low-melting polymer component to one or more polyethylene(s) and in the case of the high-melting polymer component to one or more polypropylene(s).

In a particularly preferred embodiment, the starting film web contains at least one polyethylene serving as the low-melting polymer component and at least one polypropylene serving as the high-melting polymer component.

Preferably, the low-melting polymer component contains ethylene polymers or consists of ethylene polymers, wherein both ethylene homopolymers as well as ethylene copolymers with ethylene as the main monomer as well as mixtures (blends) of ethylene homopolymers and ethylene co-polymers are suitable. Suitable ethylene homopolymers are LDPE (Low Density Polyethylene), LLDPE (Linear Low Density Polyethylene), MDPE (Medium Density Polyethylene) and HDPE (High Density Polyethylene). Preferred comonomers for ethylene copolymers are olefins other than ethylene with the exception of propylene, e.g. butene, hexene or octene. Preferably, in the case of the ethylene copolymers the comonomer content is below 20% by weight, in particular below 15% by weight. In a preferred embodiment, the low-melting polymer component consists exclusively of ethylene homopolymers, e.g. mixtures of LDPE and LLDPE, which each may be contained in amounts of 10 to 90% by weight, as well as 0 to 50% by weight of MDPE. Specific examples are a polyethylene composed of 60% by weight of LDPE and 40% by weight of LLDPE or a polyethylene of 80% by weight of LDPE and 20% by weight of LLDPE.

Besides the ethylene homopolymers and/or ethylene copolymers, the low-melting polymer component may also contain other thermoplastic polymers. There are no limits to these thermoplastic polymers, as long as, as a result thereof, the temperature, at which the total low-melting polymer component exists in the liquid molten state, does not approach too closely to the temperature at which the high-melting polymer component would be in the liquid molten state. It is also possible for the low-melting polymer component to contain a polypropylene, the melting point or melting range of which is not higher than that of an ethylene homopolymer or ethylene copolymer or although being higher than these, still being lower than the stretching temperature to be employed. As is well-known, there exists highly-crystalline isotactic, less crystalline syndiotactic and amorphous atactic polypropylene, which have different melting points, melting ranges or crystalline melting points. When using amorphous atactic polypropylene which has a considerably lower melting point or melting range than isotactic and, in some cases, even syndiotactic polypropylene, such might, in certain cases, as a function of the stretching temperature, be assigned to the low-melting polymer component.

Preferably, the high-melting polymer component contains at least one polypropylene, the melting point, melting range or crystallite melting point of which is substantially higher than that of the low-melting polymer component. A suitable polypropylene is, in particular, isotactic polypropylene. It is also possible to employ syndiotactic polypropylene, provided that its melting point, melting range or crystallite melting point is substantially higher than that of the low-melting polymer component. Suitable polypropylenes are commercially-available, for example for the manufacture of blown and/or cast films.

The high-melting polymer component may include both propylene homopolymers as well as propylene copolymers with propylene as the main monomer. In the case of propylene copolymers the content in this context of comonomers, i.e. the non-propylene, is to be considered part of the low-melting or high-melting polymer component, depending on the other components and the stretching temperature. Suitable comonomers for propylene copolymers are olefins other than propylene, preferably ethylene. In the case of propylene-ethylene-copolymers the ethylene content preferably is 2 to 30% by weight, particularly preferably 2 to 20% by weight and in particular 2 to 15% by weight, in which context, in practice, very good results are attained at an ethylene content of 3 to 20% by weight. These numerical values also apply to other olefins.

In what follows, the melting ranges for some polyethylenes and polypropylenes are listed:
LDPE: 110-114° C.;
LLDPE: 115-130° C.
HDPE: 125-135° C.;
Propylene-homopolymers: 150-165° C.;
Propylene-ethylene-copolymers: 120-162° C., even higher temperatures being possible for very low ethylene contents;
Bimodal propylene-ethylene (homo)copolymers: 110-165° C.

It is also possible to use so-called bimodal polypropylenes. In this context, these are two different polypropylenes, each with a different copolymer content, combined in one raw material. Such bimodal polypropylene has two crystallite melting points, in which case, as a rule, the approximate contents of the two polypropylenes can also be determined by DSC-analysis. As an example, a bimodal polypropylene is cited having crystallite melting points at 125° C. and 143° C. with a content of the two different polypropylenes of 25/75. At a stretching temperature of 130° C., according to the invention, the 25% polypropylene with a crystallite melting point at 125° C. would have to be assigned to the low-melting polymer component and the 75% polypropylene having a crystallite melting point at 143° C. would have to be assigned to the high-melting polymer component.

In the process according to the invention, heating of the starting film web is performed up to or above the liquid molten state of the low-melting polymer component and below the liquid molten state of the high-melting polymer component. Up to the liquid molten state means in this context that the low-melting polymer component is in a liquid molten state. It is, however, only heated to such a degree that the high-melting polymer component is not in the liquid molten state.

In a particular embodiment, a starting film web is used having the following composition: 25 to 35% by weight of an ethylene-octene-copolymer with 5 to 15% by weight of octene content; 20 to 30% by weight of a propylene-ethylene-copolymer with 3 to 12% by weight of ethylene, and the balance LDPE, based on 100% by weight of low-melting and high-melting polymer components.

Just as specific molten polypropylene can be found in the low-melting polymer component, it is also possible for a specific non-molten polyethylene to be found in the high-melting polymer component, which is then assigned to the high-melting polymer component. This is illustrated by the following example. A formulation suitable for a starting film web comprises 30% by weight of LDPE (melting point 112° C.), 30% by weight of LLDPE (melting point 124° C.), 20% by weight of HDPE (melting point 130° C.) and 20% by weight of polypropylene (melting point 160° C.). If the film web is stretched at a temperature of 126° C., the LDPE and LLDPE according to the invention are present in the liquid molten state, while not only the polypropylene, but also the HDPE are not in the liquid molten state.

In order to make it possible to conduct the process in a stable manner, even for a prolonged period of time, the (crystallite) melting points of the low- and high-melting polymer components should appropriately not be too close to one another. Preferably, the crystallite melting point of the low-melting polymer component, or, in the presence of a plurality of low-melting polymer components, the crystallite melting point of those having the highest crystallite melting point, is at least about 5° C., preferably at least about 10° C. and in particular at least about 20° C. below the crystallite melting point or the liquid molten state of the high-melting polymer component, or, in the presence of a plurality of high-melting polymer components, the crystallite melting point of those having the lowest crystallite melting point.

The process according to the invention also enables the manufacture of gas-permeable or breathable films. In this case, the films contain additional fillers, on which pores may be formed during the stretching procedure. Suitable fillers are known to the person skilled in the art. Calcium carbonate or chalk is most preferred, because of their reasonable price, but also in the light of sustainability. If a filler of more uniform particle size than chalk is desired, it is also possible to use synthetic fillers of uniform particle size or particle size distribution. In order to attain gas permeability of the film, it is appropriate that at least 40% by weight of fillers, in particular at least 50% by weight of fillers, based on the overall formulation of the starting film web (100% by weight, including filler(s)) are used. The upper limit with regard to fillers is determined in that pores are no longer formed, but holes, or that the film tears off. Suitable film formulations with fillers can be determined by the person skilled in the art on a routine basis. A formulation containing 40 to 75% by weight, in particular 50 to 75% by weight of fillers, based on 100% by weight of starting film web, is particularly suited. Care must be taken in this context not to choose the content of low-melting component so high that gas permeability is not attained or is lost again, because the pores are not generated and/or close again. In addition, it is also possible to use fillers in quantities lower than required for gas permeability of the film. Such films may be of interest in the light of sustainability. Suitable formulations are 1 to 75% by weight, in particular, 10 to 75% by weight of fillers, based on 100% by weight of starting film web.

In order attain the liquid molten state of the low-melting polymer component, but not the liquid molten state of the high-melting polymer component, the specifically-selected difference in temperature is not subject to any specific restrictions, provided the aforesaid condition has been met. The selected temperature difference is advantageously determined by practical considerations regarding safety of the process implementation, e.g. also during stretching, or by economic considerations. If, for example, the low-melting polymer component is melted at a certain temperature, further increase in temperature will not give rise to better results. Moreover, heat consumption will increase and it is possible that one comes too close to the melting range of the high-melting polymer component, such that the process is more difficult to perform. Preferably, the process of the invention is therefore performed in such a manner that heating of the starting film web is performed to 5 to 20° C., preferably 5 to 15° C. or 10 to 20° C., in particular, 10 to 15° C. or 15 to 20° C., below the crystallite melting point of the high-melting polymer component. In the alternative, heating is performed, in particular, at a temperature in the range of from 1 to 20° C., preferably 2 to 10° C., above the crystallite melting point or the liquid molten state of the low-melting polymer component(s). It must be ensured that the crystallite melting points of the low-melting polymer component(s) are attained.

The starting film webs for carrying out the process of the invention may be manufactured by any processes known according to the state of the art. For example, the starting film web may be manufactured by melting together the polymer components in the extruder at a temperature which is distinctly higher than the molten flow temperature of all components (e.g. above 200° C.) and subsequently by a slit die process or a blowing method. In the case of a slit die process, a film is extruded through a wide-slit die. The blowing method is preferred.

The starting film web may consist of one or a plurality of layers, it may also be mono- and/or co-extruded, there being no limitation with regard to the number of layers used. The layers may have identical or different formulations, in which context the assignment to the low- or high-melting polymer component is in each case determined by the crystallite melting point relative to the stretching temperature.

The starting film webs used in the process according to the invention may be pigmented, e.g. white with titanium dioxide. Furthermore, the starting film webs may contain conventional additives and processing aids. In particular, besides the already mentioned fillers, this concerns in this context pigments or other colourants, anti-adhesives, lubricants, plasticizers, processing aids, antistatic agents, germ-inhibiting agents (biocides), antioxidants, heat stabilisers, stabilisers with regard to UV-light or other agents for property modification. Typically, such substances, as in the case of fillers, are already added prior to the stretching of the starting film web according to the invention, e.g. into the polymer melt during its manufacture or prior to extruding into a film.

The thickness of the starting film web, in the case of unfilled films, is, in particular, in the range of below 30 μm, preferably below 20 μm, most preferred below 15 μm. Ranges from 10 to 20 μm and particularly preferably 10 to 15 μm are preferred. More preferably, the range is 10 to 30 μm, which corresponds to basis weights of 9 to 29 g/m$^2$, depending on the density. In gas-permeable starting films (filled films), preferred basis weights are in the range below 50 g/m$^2$, in particular below 40 g/m$^2$, particularly preferably below 30 g/m$^2$ and more preferably below 20 g/m$^2$.

According to the invention, heating of the starting film web is performed by means of at least one heating roller. Preferably, heating is performed by means of one or more heating rollers, which may be contact rollers being heated to the predetermined temperature by a heat carrier, such as steam, water, oil. In a preferred embodiment a single heating or contact roller is employed. It is, however, also possible to use two or more heating rollers, in which case it is necessary to ensure that the liquid molten state of the low-melting polymer component is attained upstream of the cooling roller nip. In order to ensure that the starting film web does indeed attain the temperature of the heating roller or that, in the case of high production velocities, (where the surface temperature of the heating cylinder is higher than that of the film), the liquid molten state of the low-melting polymer component is attained with certainty, an adequate residence time of the starting film web on the heating roller surface must be ensured. This can be attained by an appropriate wrapping path of the heating cylinder and thus the size of the wrap angle α (see FIGURE), the diameter of the heating roller and/or the film web velocity as a function of the film thickness. In addition, other heating methods such as radiant heat, e.g. with infra-red radiators, may be used. Due to its partially liquid molten state, the film web adheres more strongly to the roller, which results in a shift of the detachment point in the direction of rotation of the heating roller and which means an enlargement of the detachment angle β (see FIGURE). In order to permit detachment of the film web from the heating roller and, consequently, to prevent tearing-off of the film web, it is appropriate for a heating roller to be used which is provided with an anti-adhesion coated surface, having reduced adhesion properties in relation to the partially liquid molten film web. For this purpose, one uses, for example, a PTFE (polytetrafluoroethylene)-coated heating roller.

According to the invention, the film is stretched between at least one heating roller and the cooled roller nip. In the present invention the term "stretching" has the same meaning as "drawing out" or "extending". The term "stretching ratio" likewise has the same meaning as "extension ratio" or "drawing out ratio". Stretching, extending or drawing out a film means lengthening the film in the determined direction, which results in a reduction of the film thickness. According to the invention, the film is stretched in the direction of the machine or in longitudinal direction (md), for example by varying the velocity of the heater and cooling rollers. A stretching ratio of 1:1.5 means, for example, that the film thickness is reduced from, for example, 15 µm to 10 µm. According to the invention it is essential that the film web is in the partially-molten state during the stretching procedure.

The stretching ratio depends on the film formulation and the selected process parameters and is preferably at least 1:1.2, more preferably at least 1:1.5, in particular, at least 1:2, even more preferably at least 1:2.5, more preferably at least 1:3, or at least 1:4.

In a preferred embodiment of the invention, the stretching is brought about in that the cooling rollers forming the cooled roller nip are driven at a higher velocity than the heating roller. In another preferred embodiment of the invention, two or more rollers, of which at least two are driven at different velocities, are provided upstream of the cooling roller nip such that the film web is extended between these two rollers, and in which case at least the first of the two or more rollers is designed as a heating roller. It is also possible for the second and, where applicable, the further rollers to be likewise designed as a heating roller. In particular, if a plurality of rollers are provided, it is, however, also possible for one of the rollers to be designed as a cooling roller. A cooling roller brings about cooling of the film web on one side and results, therefore, in slow cooling of the film. In contrast thereto, the cooling roller nip provided according to the invention, due to the two cooling rollers, provides cooling of the film web on both sides, thereby causing fast cooling. If one cooling roller is employed, heating to the partially-molten state of the film web upstream of the cooling roller nip is again necessary, which can appropriately again be performed by a heating roller. Arrangements such as heating roller—heating roller—cooled roller nip or heating roller—cooling roller—heating roller—cooled roller nip are possible.

It is also possible to additionally subject the film web to transverse drawing out. Such biaxial drawing out can, for example, be attained by commercially-available stretching or extension machines, e.g. those sold by the company Brückner. Care must be taken in this case, that the partially liquid molten state according to the invention is maintained during the stretching process.

In the process according to the invention for the manufacture of a non-woven fabric-film laminate at least two heating rollers are provided upstream of the cooled roller nip, which are driven at different velocities, such that the film web is stretched between both rollers. In addition, a non-woven fabric web is moving towards the second of the two heater rollers, in which case either the film web or the non-woven fabric web can contact the heater roller. It is also possible to feed a plurality of non-woven fabric webs. Such thermo-laminating process can be performed, for example, as described in WO 2006/024394. Similarly to what is described above for stretching the film, it is possible for thermo-laminating as well to provide a cooling roller between the at least two heating rollers, in particular, if more heating rollers are present. In the case of thermo-lamination, the starting film web is heated, jointly with a starting non-woven fabric web, the melting point of which is above the crystallite melting point of the polymer material of the starting film web, to a temperature above the crystallite melting point of the polymer material of the starting film web and below the melting point of the starting non-woven fabric web. The polymer material of the starting film web designates in this context the low-melting polymer component and, depending on the morphology and the chemical composition of the starting non-woven fabric web, possibly additionally the high melting polymer component as a whole or part thereof. The chemical composition of the polymer material of the starting film web should be adapted to the chemical composition of the non-woven fabric web, i.e. the melting points and raw materials should be adapted to one another. Just as described in WO 2006/024394, the webs to be laminated should have a similar morphology in at least one formulation component, such that adequate adhesive bonding can be attained. In the present case, this means that the heating roller onto which the starting non-woven fabric web is fed, heats the starting film web in such a manner that the polymer component which brings about bonding, is in the liquid molten state. The temperature of the heating rollers during stretching and thermo-laminating may thus differ as a function of the composition of the starting film web and the starting non-woven fabric web, in particular, the heating roller onto which the non-woven fabric web is fed, may have a higher temperature. This can be elucidated by way of the following example. If the starting non-woven fabric web used is based on a polypropylene and has a melting point in the range of from 160 to 165° C., the polymer material of the starting film web should have a polypropylene as the adhesive component which is in the liquid molten state, regardless of whether this polypropylene belongs to the low- or high-melting polymer component of the starting film web during stretching. In this case, adequate adhesion would normally not be ensured, if there is only one polyethylene in the liquid molten state. If applied to a starting film formulation with 35% by weight of LDPE (melting point 112° C.), 20% by weight of LLDPE-butene (melting point 121° C.), 10% by weight of polypropylene (melting point 162° C.), 30% by weight of random-polypropylene-copolymer (melting point 140° C.) and 5% by weight of $TiO_2$-white-concentrate, pigment and additives, the components being the same as those listed in the example at the bottom of Table I, this would mean that during the thermo-laminating procedure the LDPE, the LLDPE-butene and the random-polypropylene-copolymer (melting point 140° C.) are in the liquid molten state, whereas the polypropylene (melting point 162° C.) is not. That is to say, the heating roller to which the non-woven fabric web is fed, must ensure appropriate heating of the starting film web, for example to 142° C. or 143° C. At this temperature, adequate adhesion to the polypropylene non-woven fabric is attained without any risk of melting initiation of the non-woven fabric. Stretching, on the other hand, is performed at a lower temperature, for example at 124° C., such that the LDPE and the LLDPE-butene are in the liquid molten state, but not the polypropylene (melting point 162° C.) and the random-polypropylene-copolymer (melting point 140° C.).

The starting non-woven fabric web is manufactured in a manner known per se and is based, like in WO 2006/024394, on thermoplastic polymers, e.g. fibres of PE, PP, polyester (PET), rayon, cellulose, polyamide (PA) or mixtures thereof. Particularly preferred are e.g. non-woven fabrics of spinnable or staple fibres based on PP, PE or PET, as well as non-woven fabrics consisting of mixtures of PP and PE or mixtures of PET and PP or PE. It is also possible to use two- or multi-layered non-woven fabrics.

According to the invention, the film web is passed through a cooled roller nip after heating. When manufacturing a non-woven fabric-film laminate, the film web and the non-woven fabric web are passed jointly through the cooled roller nip after heating and are bonded to one another. The rollers forming the cooling roller nip are cooled in such a manner that rapid and sudden cooling is attained. Cooling to a temperature below the crystallite melting point of the low-melting polymer component, preferably to at least 5° C. below that melting point, in particular to at least 10° C. below that melting point, is appropriate. Preferred cooling ranges are 5 to 10° C., more preferably 10 to 30° C. below the crystallite melting point of the low-melting polymer component. Cooling of the rollers with water may, for example, take place in a temperature range of 5 to 20° C., e.g. water having a temperature of about 10° C. The spacing between the last heating roller and the cooling roller nip should in this context not be too wide, due to possible heat loss, in which context a minimum spacing is defined by the dimensions of the rollers. The cooling roller nip may in the simplest case be, for example, a smooth-roller nip with two smooth rollers. In the case of hygiene films the roller nip is however formed preferably by a pair of rollers with one texturing roller and one smooth roller, thereby imparting to the film web a textured surface. Preferred textures in the hygiene field are micro-textures, e.g. a truncated pyramid. Preferably, the cooled roller nip consists of a steel roller and a rubber roller operating under counter-pressure, the steel roller being provided with the textured surface.

According to the invention, the velocity of the rollers forming the cooling roller nip may be so selected that the said velocity is higher than that of the heating roller or, if more heating rollers are used, is higher than that of the last heating roller, such that the film is stretched between them. Alternatively or additionally, as described above, it is also possible to stretch the film between two rollers upstream of the cooling roller nip. This embodiment is of particular interest in the event that the spacing between the heating roller and the cooling roller nip is to be kept as narrow as possible, in order, for example, to prevent constrictions in the course of the stretching procedure. The stretching procedure is then performed between two heating rollers, the spacing relationship of which may be decreased arbitrarily. The stretched film is then passed from the second heating roller into the cooling roller nip without any further stretching or with lesser further stretching.

Depending on the film parameters and other process conditions, the film web velocities are in the range of 50 to 900 m/min. The velocity of the heating roller(s) is preferably 50 to 600 m/min, in particular 100 to 400 m/min. The velocity of the rollers forming the cooling roller nip is preferably 75 to 900 m/min, in particular 150 to 600 m/min. The velocities of the heating roller(s) and the cooling rollers are selected such that, depending on the film formulation and the selected process parameters, the desired stretching ratio is attained.

The process according to the invention enables the manufacture of films having a very thin film thickness of e.g. 10, 8, 6 or even only 5 μm. Preferred, unfilled films have a thickness in the range of 2 to 13 μm or have a basis weight of 1 to 15 g/m². Filled films preferably have the same basis weight values.

Despite being very thin and soft (haptically-attractive), the films obtained according to the invention have excellent mechanical properties and, in addition, still have a very high puncture resistance (i.e. resistance to super-absorber granules, e.g. in diapers) and high thermo-stabilities (i.e. resistance to hot melt-adhesives). It was surprising that it is possible at all to manufacture such thin films.

Films obtained according to the invention may be further processed in a manner known per se, in which context the manufacture of non-woven fabric-film laminates is particularly preferred. For manufacturing such laminates, the latter may be adhesively-bonded by adhesive agents, preferably in-line. Apart from that, non-woven fabric-film laminates may also be manufactured by thermo-bonding, known to the person skilled in the art, in which case the material of a film and/or non-woven fabric obtained according to the invention is melted by high temperature and pressure at particular points between two heated rollers, in most cases an embossing roller (embossed steel roller) and a smooth steel roller serving as counter-roller, thereby causing the film and non-woven fabric to be bonded together. Moreover, non-woven fabric-film laminates, as described above, may also be manufactured by thermo-laminating. Thermo-laminating is particularly preferred in the case of very thin films, e.g. 4 g/m². The non-woven fabric-film laminates produced may be further processed in a manner known per se, in which case stretching in the machine or transverse direction or in both directions is likewise possible.

The FIGURE shows a preferred embodiment for performing the process according to the invention, wherein the stretching is attained by a velocity of the rollers forming the cooled roller nip which is higher than that of the heating roller. From a roller 1 a starting film web 2 is passed over deflecting rollers 3 and 4 and a pressing roller 5 onto a heating roller 6. The heating roller 6 may be, for example, an anti-adhesively coated steel roller, which is heated to the desired surface temperature by heat supply. The film web then runs on the heating roller 6, thereby being heated according to the invention. The wrap angle α is that angle which is formed between the first point of contact of the starting film web 2 with the heating roller 6 and that point, viewed in the direction of rotation of the heating roller 6, at which the detachment of the film web from the heating roller comes about. From the heating roller 6 the film web, at the point of detachment A, runs at a detachment angle β into a cooling roller nip, formed by the rollers 7 and 8. The roller 8 is preferably designed as a textured roller, thereby imparting a textured surface to the film web. The roller pair 7/8 is preferably water-cooled, e.g. with water having a temperature of about 10° C. The rollers 7 and 8 forming the cooling nip are driven such that a higher velocity arises in relation to the web velocity of the heating roller 6, so that the desired degree of stretching is attained. In this context, a stretching ratio between the heating roller and the roller nip causes a reduction of the detachment angle β. The film is taken off downstream of the roller pair 7/8.

The invention, due to the manufacture of films having extremely thin thicknesses, enables raw material savings, thereby contributing to saving resources and sustainability. As a result, it contributes to protecting the environment. This applies, in particular, to films in the hygiene sector, where the films are used to a large extent as components of disposable products.

The films and non-woven fabric-film laminates obtained according to the invention are used in the hygiene or medical fields, e.g. as clothing-protection film or generally as a liquid-impermeable barrier layer, in particular as back sheets in diapers, sanitary napkins, mattress protectors or in similar products.

The invention is elucidated in detail by way of the following example.

EXAMPLE

A starting material film web with a formulation according to Table 1 was manufactured according to the blowing method, the film containing the polypropylene with the lower melting point (140° C.) having been coextruded to serve as the outer layer.

TABLE 1

Film formulation

| Amounts in parts by weight | Component | Crystallite melting point ° C. |
|---|---|---|
| 55 | LDPE | 112 |
| 20 | LLDPE-butene[1] | 121 |
| 10 | Polypropylene | 162 |
| 10 | Random-polypropylene-co-polymer[2] | 140 |
| 5 | TiO$_2$-White-concentrate, pigment and additives | — |

[1]MFR 1.0 at 190° C./2.16 kg
[2]Propylene-ethylene-copolymer with 10% by weight of ethylene The conditions when blowing the film tube are apparent from Table II below.

TABLE II

Blowing conditions

| Annular die | 550 mm diameter |
|---|---|
| Die nip | 1.2 mm |
| Tube diameter | 1590 mm |
| Basis weight of film | 14 g/m$^2$ |
| Extruder temperature | 240° C. |

The film tube obtained was cut open in longitudinal direction and wound onto two rollers. The film width was 2.5 m.

This starting film web was subjected to the process shown in the FIGURE as follows. After taking off the starting film web 2 from the roller 1, it passes via the deflecting rollers 3, 4 and the pressing roller 5 onto the heating roller 6. The heating roller (HZ) 6 is an anti-adhesively coated steel roller, which is heated by heat supply to a surface temperature according to Table III. The heating roller 6 is driven at a web velocity of 100 m/min. From the heating roller 6 the film web passes into the cooling roller nip formed by the roller pair 7/8, which is driven at a web velocity which is higher than the heating roller, depending on the desired degree of stretching. The velocity difference between heating roller and cooling nip results in the degree of stretching. For example, a heating roller velocity of 100 m/min and a cooling roller velocity of 300 m/min bring about a stretching ratio of 100:300 or 1:3. The roller 8 is designed as a smooth roller or as a roller with a textured surface. The roller pair 7/8 is water-cooled (approximately 15° C.). The rollers 7/8 forming the nip are driven in such a manner that the stretching ratios set out in Table III below are attained. This made it possible to obtain films having the basis weights stated in Table III. Table III also shows tests, in which heating was insufficient, thereby causing tearing off of the films.

TABLE III

| Heating roller (HZ) temperature | Stretching ratio | Production at >5 min | Basis weight [g/m$^2$] |
|---|---|---|---|
| 105° C. | 1:1.50 | tearing | — |
| 117° C. | 1:2.00 | possible | 7.0 |
| 117° C. | 1:3.50 | tearing | — |
| 124° C. | 1:3.50 | possible | 4.0 |

Surprisingly, it was found that stretching ratios higher than 1:1.50 are possible as soon as the starting film web is in the liquid molten state of the lowest-melting polyethylene-component (LDPE) during the stretching process. Thus, at a stretching temperature (surface temperature of the heating cylinder) of 117° C. (55% LDPE-content in the liquid molten state) is was possible to obtain a stretching ratio of 1:2.0, i.e. a 14 g/m$^2$ starting film was able to be stretched to 7.0 g/m$^2$. At a stretching temperature of 124° C. (55% LDPE- and 20% LLDPE-content in the liquid molten state) it was even possible to obtain a stretching ratio of 1:3.5, i.e. a 14 g/m$^2$ starting film was able to be stretched to 4.0 g/m$^2$.

The example shows that the process according to the invention enables the manufacture of films having very low basis weights.

The thin films obtained can subsequently be bonded to non-woven fabrics to form laminates for the purpose of improved handling. Suitable processes are adhesive bonding. In the alternative, thermo-lamination, as described above, may be performed, in which case the non-woven fabric is laminated onto the outer polypropylene layer.

The invention claimed is:

1. A process for the manufacture of a non-woven fabric-film laminate, the process comprising:
heating of a starting film web of thermoplastic polymer material, the thermoplastic polymer material comprising at least one low-melting polymer component and at least one high-melting polymer component, to an at least partly molten state in which the at least one low-melting polymer component exists in a molten liquid state and the at least one high-melting polymer component does not exist in the molten liquid state, by a first heating roller, and
passing the partly molten film web to a second heating roller,
wherein the first and second heating roller are operated at different velocities, so that the film web is stretched between the first and the second heating roller, and wherein, additionally, a non-woven fabric web is passed over the second heating roller and is passed through a cooled roller nip together with the film web, wherein the melting point of the non-woven fabric web is above the crystallite melting point of the at least one low-melting polymer component and optionally, the at least one high-melting component of the starting film web, and
wherein the film web is heated, jointly with the non-woven fabric web, to a temperature in which the at least one low-melting polymer component and optionally, the at least one high-melting polymer component as a whole or part thereof, of the starting film web exist in the molten liquid state and below the melting point of the non-woven fabric web by the second heating roller.

2. The process according to claim 1, wherein the film web is stretched at a stretching ratio of at least 1:1.5.

3. The process according to claim 1, wherein the film web is stretched at a stretching ratio of at least 1:2.

4. The process according to claim 1, characterized in that the starting film web contains 50 to 75% by weight of filler.

5. The process according to claim 1, wherein the starting film web comprises 15 to 85% by weight of the low-melting polymer component and 85 to 15% by weight of the high-melting polymer component, based on 100% by weight of the low-melting and the high-melting polymer components.

6. The process according to claim 1, wherein at least one of the low-melting polymer components comprises polyethylene and at least one of the high-melting polymer components comprises polypropylene.

7. The process according to claim 1, wherein the heating of the starting film web is performed up to 5 to 20° C. below the crystallite melting point of the at least one high-melting polymer component by the first heating roller.

8. The process according to claim 1, wherein the film web is stretched at a stretching ratio of at least 1:1.2.

9. The process according to claim 1, wherein the film web is subjected to cooling in the cooled roller nip to at least 10 to 30° C. below the crystallite melting point of the at least one low-melting polymer component.

10. The process according to claim 1, wherein the starting film web contains 1 to 75% by weight of filler.

11. The process according to claim 10, wherein the filler is chalk.

\* \* \* \* \*